United States Patent [19]

Meunier et al.

[11] Patent Number: 5,236,914

[45] Date of Patent: Aug. 17, 1993

[54] DERIVATIVES OF METALLOPORPHYRINS AND APPLICATION THEREOF FOR THERAPEUTIC PURPOSES AND IN PREPARING HYBRID MOLECULES

[75] Inventors: Bernard Meunier, Castanet; Guita Etemad-Moghadam; Li Ding, both of Toulouse; Suzy Cros, Ramonville St Agne, all of France

[73] Assignee: Centre National de la Recherche Scientifique (CNRS), Paris, France

[21] Appl. No.: 613,638

[22] PCT Filed: Jun. 2, 1989

[86] PCT No.: PCT/FR89/00273

§ 371 Date: Nov. 28, 1990

§ 102(e) Date: Nov. 28, 1990

[87] PCT Pub. No.: WO89/12049

PCT Pub. Date: Dec. 14, 1989

[30] Foreign Application Priority Data

Jun. 2, 1988 [FR] France ............... 88 07372

[51] Int. Cl.$^5$ .................. A61K 31/40; C07D 487/22
[52] U.S. Cl. .......................... 514/185; 540/145
[58] Field of Search .............. 540/145; 514/184, 185

[56] References Cited

U.S. PATENT DOCUMENTS

| | | | |
|---|---|---|---|
| 2,740,794 | 4/1956 | Bonner | 540/145 |
| 4,386,087 | 5/1983 | Lavallee | 540/145 |
| 4,614,723 | 9/1986 | Schmidt et al. | 540/145 |

FOREIGN PATENT DOCUMENTS

| | | |
|---|---|---|
| 0118913 | 9/1984 | European Pat. Off. |
| 0186962 | 1/1986 | European Pat. Off. |

Primary Examiner—Thurman K. Page
Assistant Examiner—Jyothsna Venkat
Attorney, Agent, or Firm—Young & Thompson

[57] ABSTRACT

Metalloporphyrin derivatives of the formula

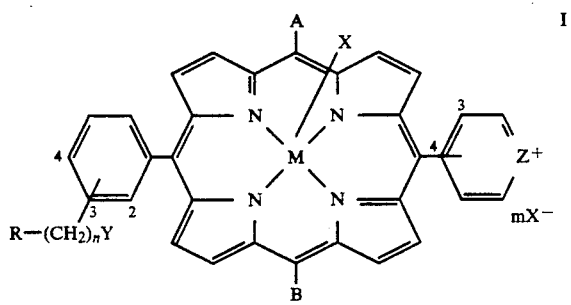

in which A and B each represents:

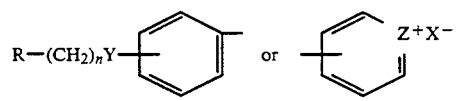

and

Z$^+$ represents N$^+$—R$_1$ or C—N$^+$R$_1$R$_2$R$_3$, R$_1$ being C$_1$-C$_{10}$ linear or branched aliphatic, and R$_2$ and R$_3$ each being hydrogen or C$_1$-C$_{10}$ linear or branched aliphatic, R represents NH$_2$, OH, COOH or —N(R$_1$)$_3$ group or a halogen, n is 0 or an integer from 1 to 10, the corresponding alkylene group being either linear or branched, M represents Fe or Mn, and X represents the anion of a pharmaceutically acceptable carboxylic acid, m being an integer from 1 to 5, and Y represents a bond or a —O—, —CO— or —CONH— radical.

The compounds have antitumoral and antiviral utility.

6 Claims, 1 Drawing Sheet

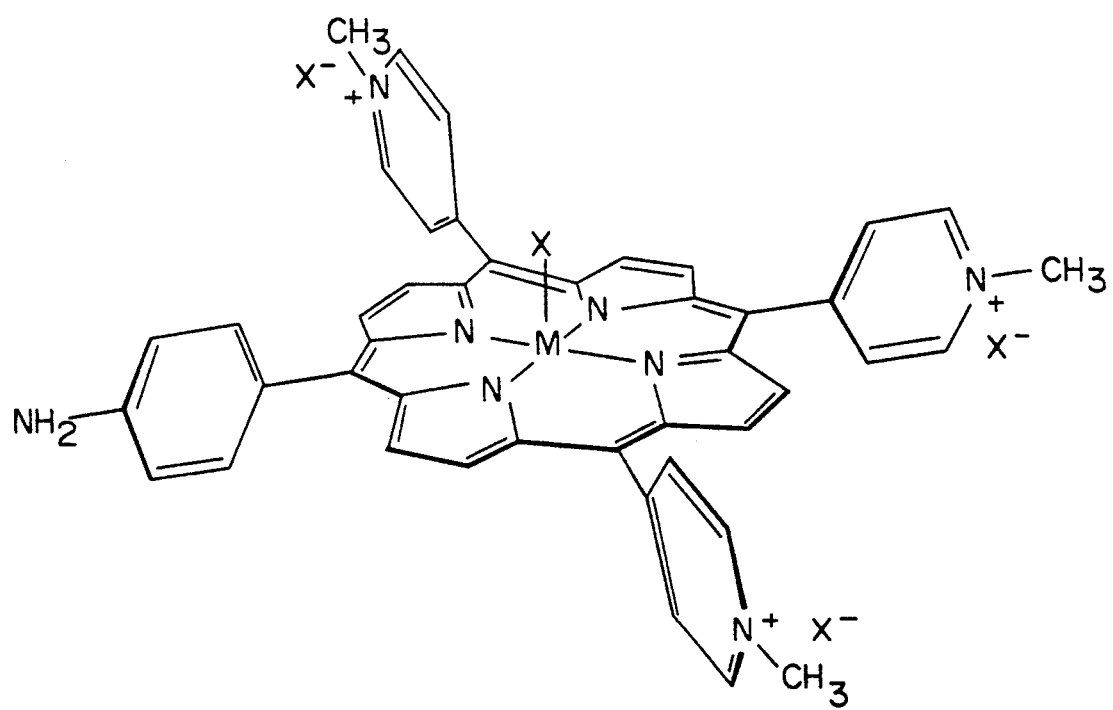

DERIVATIVES OF METALLOPORPHYRINS AND APPLICATION THEREOF FOR THERAPEUTIC PURPOSES AND IN PREPARING HYBRID MOLECULES

The subject of the present invention is novel derivatives of metalloporphyrins, their preparation, their application in therapy, and their use for the preparation of hybrid molecules for therapeutic use.

The use of certain hemtoporphyrin derivatives in the treatment of cancers by means of phototherapy has been described, for example, by J. Moan (Photobiol. Photochem. 43, 681 (1986). These molecules possess the characteristic of accumulating at the site of tumors, which makes it possible to use them as biological markers or therapeutic agents. However, the preparation of these derivatives often leads to a mixture of products not always well defined and of variable composition. This established fact justifies the development of porphyrin derivatives prepared by total synthesis and which can be substituted for hematoporphyrins in the treatment of cancers by phototherapy.

Moreover, recent experiments have shown that metalated derivatives of synthetic porphyrins are capable of cleaving nucleic acid (DNA) in vitro by means of an oxidative process (EP-A-118 913; E. Fouquet, G. Pratviel, J. Bernadou and B. Meunier, J. Chem. Soc., Chem. Commun., 1169 (1987). This nuclease activity of water-soluble metalloporphyrins is of a special interest because it can be observed at very low concentrations of the reagents (of the order of $10^{-6}$ to $10^{-8}$M), lower than those of bleomycin (an antitumoral antibiotic possessing high nuclease activity in the presence of ferric ions, molecular oxygen and reducers). The numerous studies carried out in recent years on the molecular pharmacology of this important drug in anticancer chemotherapy indicate that its cytotoxic and antitumoral activity may be due to its capacity to degrade the DNA of tumor cells.

According to EP-A-0,186,562, tetra-(substituted phenyl)-porphyrins are provided, which are useful in the treatment and the localization of tumors, According to the present invention the synthesis of metalloporphyrins has been carried out (the coordination sphere of which around the iron or magnesium ions mimics the arrangements of the peptide ligands of bleomycin) having the two following properties:
- nuclease activity toward DNA in vitro, and
- cytotoxic activity on whole cells, which, to the knowledge of the inventors, have not yet been described for metalloporphyrins. Thus, the invention relates to novel porphyrin derivatives possessing this dual property. Furthermore, it is also shown that this dual property is conserved in hybrid molecules when the porphyrin skeleton is linked to an entity possessing an affinity for the nucleic acids and also capable of modulating the biological activity of these cytotoxic metalloporphyrins (polyamines, polylysine, oligonucleotides . . . ).

The novel metalloporphyrin derivatives according to the invention correspond to the general formula:

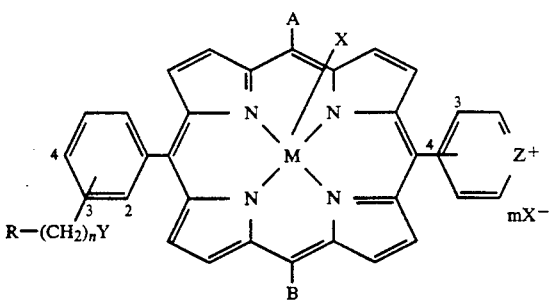

in which A and B each represents:

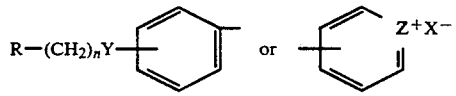

$Z^+$ represents $N^+$—$R_1$ or $C$—$N^+R_1R_2R_3$; $R_1$ being $C_1$-$C_{10}$ linear or branched aliphatic, and $R_2$ and $R_3$ each being hydrogen or $C_1$-$C_{10}$ linear or branched aliphatic, R represents $NH_2$, OH, COOH or —$N^+(R_1)_3$ group or a halogen, n is 0 or an integer from 1 to 10, the corresponding alkylene group being either linear or branched, M represents a transition metal, and $X^-$ represents the anion of a pharmaceutically acceptable carboxylic acid, m being an integer from 1 to 5 and Y represents a bond, or a —O—, —CO— or —CPNH— radical.

Preferably, $R_1$ represents an alkyl group, in particular methyl or ethyl, and $R_2$ and $R_3$ each represents a hydrogen atom or methyl, M represents in particular Cr, Mn, Fe, Co, Ni, Cu, Zn or Ru, and preferably Mn or Fe.

$X^-$ is selected in particular from the anions of the soluble carboxylic acids commonly used in pharmacy, in particular: acetate, propionate, butyrate, ascorbate, benzoate, cinnamate, citrate, fumarate, glycolate, malonate, tartrate, malate, maleate and mandalate.

Preferably, $Z^+$ is $N^+$—$R_1$.

The compounds of formula I can be prepared by
a) condensation of a phenyl-carboxyaldehyde of formula:

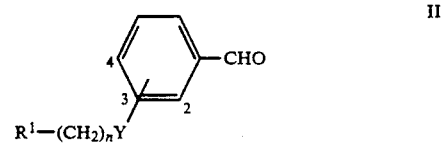

in which n and Y have the same meanings as in formula I and R' is the R group of formula I, protected if appropriate, with an aldehyde of formula;

in which Z' is selected from N or

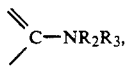

$R_2$ and $R_3$ have the same meanings as in formula I, and with pyrrole in acid medium so as to obtain a porphyrin (PP) tetrasubstituted at positions 5, 10, 15 and 20 of the general formula:

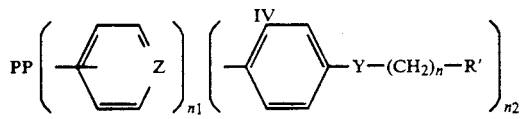

in which R', n, Y and Z' have the same meanings as in the formulae II and III, respectively, and $n_1$ and $n_2$ are integers from 1 to 3, with $n_1+n_2=4$, b) if necessary, the compound IV is subjected to a deprotection of the R' radical in order to given rise to a porphyrin tetrasubstituted at 5, 10, 15, 20 of the general formula:

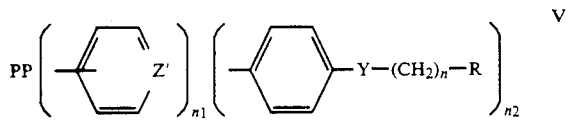

in which Z' has the same meaning as in formula III, PP, $n_1$ and $n_2$ are as in formula IV and n, R and Y have the same meanings as in formula I.

c) the compound of formula V, after optional protection of R, is subjected to an alkylation reaction, by means of a halide $R_1$-hal, $R_1$ having the same meaning as in formula I and hal indicating bromide or iodine, so as to give rise to a porphyrin tetrasubstituted at 5, 10, 15, 20 of the general formula:

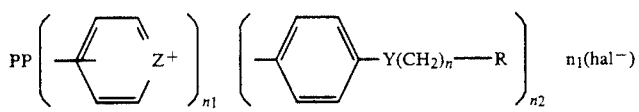

and d) this compound is metalated with the aid of a salt MXp, M and X having the same meanings as in formula I and p corresponding to the valency of the metal M.

The step a) is carried out in acid medium, in particular in propionic acid at reflux in the presence of acetic anhydride.

Depending on the nature of the radical R, protection may be necessary, if $R=NH_2$, $R'=NO_2$ will be selected and then step b) will consist of reducing $NO_2$ to $NH_2$, in particular by mean of stannous chloride in a strong acid medium. If R=COOH, R' will be selected from a corresponding alkyl ester and step b) will consists of hydrolyzing this ester.

The alkylation step c) is carried out in a conventional manner in a neutral polar solvent such as dimethylformamide (DMF) at reflux.

The metalation step d) can also be carried out in DMF at reflux, in particular in the presence of 2, 4, 6-collidine.

According to an alternative, the steps c) and c) can be carried out in the reverse order.

The invention also relates to the use of the compounds (I) for the preparation of hybrid molecules for therapeutic use, comprising, for example, a metalloporphyrin (I) linked to an intercalating agent such as 9-methoxy-ellipticine, which makes it possible to prepare molecules having the biological activity of each of the two components.

The following examples illustrate the invention.

The nuclear magnetic resonance spectra were recorded on a Bruker 250 WM FT apparatus. The mass spectra were recorded either on a Ribermag R1010 apparatus for the DCI spectra ($NH_3$), a Varian Mat 311A for filed desorption spectra or a ZAB for the FAB spectra and the IV-visible spectra were recorded on a Varian-Cary 2300 apparatus.

BRIEF DESCRIPTION OF THE DRAWINGS

FIG. 1 is 5-(4-aminophenyl)-10,15,20-tris(N-methyl-4-pyridyl)porphyrin salt.

EXAMPLE 1

Manganese (III) 5-(4-Nitrophenyl)-10, 15, 20-Tris (N-Methyl-4-Pyridyl)-Porphyrin Pentaacetate and Related Derivatives a) 5-(4-nitrophenyl)-10, 15, 20-tris (4-pyridyl)-porphyrin.

A mixture of 3 g (0.020 mole, 1.75 eq.) of 4-nitrophenyl carboxaldehyde in 158 ml of propionic acid and 8 ml of acetic anhydride is heated at 110° C. with stirring. To this solution is added slowly 3.2 ml (0.034 mole, 3 eq.) of pyridine-4-carboxaldehyde followed by 3.1 ml (0.045 mole, 4 eq.) of pyrrole and the mixture is refluxed for 1 h 30. After being allowed to attain ambient temperature, the mixture is evaporated to dryness and neutralized with an aqueous solution of ammonia. After filtration, The precipitate is washed several times with dichloromethane. The organic phase is then concentrated and then purified on a column of dry silica (eluant: dichloromethane followed by dichloromethane/ethanol: 95/5). Product isolated=0.526 g; yield =7,.1%.

TLC:RF=0.51 (eluant:$CH_2Cl_2$/EtOH 95/5).

UV-visible ($CHCl_3$)λ(ε): 640 (1.1×$10^3$); 586 (2.0×$10^3$); 546 (2.8×$10^3$); 512 (6.7×$10^3$); 418 (1.6×$10^5$) (Soret band).

$^1$H NMR ($CDCl_3$): δ:9.06 (d, 6H, J=5.9 Hz, β-pyrrole; 8.66 (d, 2H, J=8.60 Hz, 4-nitrophenyl 2,6-protons); 8.38 (d, 2H, J=8.60 Hz, p-3.5 of 4-nitrophenyl); 8.15 (d, 6H, J=5.9 Hz, 3.5 pyridine protons); −2.89 (s, 2H, NH pyrrole). Analysis : (the calculations assume the presence of one molecule of f water of solvation) $C_{41}H_{26}N_8O_2$, $H_2O$.

| Analysis: (the calculations assume the presence of one molecule of water of solvation) $C_{41}H_{26}N_8O_2$, $H_2O$ | | | |
|---|---|---|---|
| | C | H | N |
| Calculated % | 72.34 | 4.15 | 16.46 |
| Found % | 72.87 | 4.06 | 16.93 | b) 5-(4-aminophenyl)-10, 15, 20-tris (4-pyridyl) porphyrin

To 0.25 g (0.38 mmole) of the porphyrin (a) in 18 ml of 6N hydrochloric acid are added 0.672 g (3 mmoles, 8 eq.) of stannous chloride dihydrate and the mixture is stirred at ambient temperature for 15 h. The mixture is then neutralized with 1N sodium hydroxide, then extracted with dichloromethane. The organic phase is washed with water, then dried over magnesium sulfate. The solvent is evaporated to dryness. The residue is taken up in dichloromethane and precipitated by the addition of hexane ($CH_2Cl_2$/hexane:1/10), then filtered off and dried in a vacuum.

Product isolated=0.21 g; yield=87%.

UV-visible ($CHCl_3$)$\lambda(\epsilon)$: 652 (3.0×10$^3$); 590 (3.2×10$^3$); 554 (4.5×10$^3$); 515 (7.8×10$^3$); 420 (8.8×10$^4$) (Soret band).

Mass (DCI) : M$^+$=633 and (FD) : M$^+$—H=632

$^1$N NMR (DMSOd$_6$ at 303K) $\delta$ : 9.15 (d, 6H, J=5.50 Hz, p-3,5-pyridine); 7.99 (d, 2H, J=8.20 Hz, p-2,6 of 4-aminophenyl); 7.14 (d, 2H, J=8.30 Hz, p-3,5 of 4-aminophenyl); 5.87 (s, 2H, $NH_2$); −2.80 (s, 2H, NH pyrrole).

c) 5-(4-benzoylaminophenyl)-10, 15, 20-tris(4-pyridyl)-porphyrin. 0.010 ml (0.086 mmole, 1.8 eq.) of benzoyl chloride is added dropwise to a solution of 0.030 g (0.047 mmole) of porphyrin (b) in 3 ml of anhydrous pyridine maintained in an ice bath. The mixture is stirred for 1 h at 0° C. After this time the solvent is evaporated to dryness and the residue is taken up with dichloromethane. This solution is washed with distilled water, 5% sodium hydroxide solution, then with distilled water. The organic phase is dried over magnesium sulfate, then evaporated to dryness. The residue is dried under vacuum. The product isolate=0.025 g; yield=71%. $^1$H NMR (DMSOd$_6$ at 297K) $\delta$ 10, 72(s, 1H,NH); 8.96 (d, 6H, J=5.3 Hz), protons 2,6 pyridine); 8.93 (d, 2H, J=4.7 Hz, $\beta$-pyrrole; 8.83 (n, 4H, $\beta$-pyrrole); 8.82 (d, 2H, J-4.7 Hz, $\beta$pyrrole); 8.22 (m, 10H, protons 3,5 pryidine and phenyl); 8.11 (d, 2H, J=8.0 Hz, protons-2,6-4-aminophenyl); 7.65 (m, 3H, protons-3,5-4-amino-phenyl, para-phenyl); −2.85 (s, 2H, NH pyrrole).

d) Manganese (III) 5-(4-aminophenyl)-10, 15, 20-tris (N-methyl-4-pyridyl) porphyrin pentaacetate.

To 0.030 g (0.05 mmole) of porphyrin (c) in 3 ml of DMF, are added 0.062 ml (0.047 mmole, 10 eq.) of 2,4,6-collidine followed by 0.047 mmole of a salt of manganese e.g. Mn ($CH_3COO$)$_2$, $4H_2O$ (or of iron or zinc). The mixture is refluxed for three hours and then stirred at ambient temperature for 15 hours. The solvent is evaporated to dryness and the residue is washed with water then purified on a dry column of neutral alumina (eluant:dichloromethane followed by dichloromethane/ethanol). To the metalloporphyrin thus obtained in 3 ml of DMF, methyl iodine (10 eq.) is added and the mixture is stirred at ambient temperature for 15 hours. The mixture is then evaporated to dryness. Deprotection of the amine group is carried out by addition of a solution of 9M ammonia. The mixture is then stirred for 3 hours at 70° C. then for 15 hours at ambient temperature. After this time, the mixture is evaporated to dryness, then treated with 6M hydrochloric acid, evaporated to dryness and taken up in methanol.

The addition of anhydrous ion exchange resin of the Amberlite IRN78 type in the acetate form (4 eq.) to this solution, followed by stirring for three hours at ambient temperature leads to the acetate derivative of the title after filtration followed by evaporation of the solvent. The product is then purified by trituration with ether.

The corresponding iron, zinc and nickel derivatives were prepared in the same manner by replacing manganese acetate by $FeCl_2$. $4H_2O$, $Zn(CH_3COO)_2$, $2H_2O$, or $NiCl_2$, $6H_2O$ respectively (10 eq. each time). Yields 60–70%.

Manganese derivative: UV-visible ($H_2O$ at 7.73×10$^{-6}$M) $\lambda(\epsilon)$ 596 (3.9×10$^3$); 554 (8.6×10$^3$); 464 (7.5×10$^3$).

Zinc derivative: UV-visible ($H_2O$ at 23.9×10$^{-6}$M) $\lambda(\epsilon)$ 606 (2.5×10$^3$) 562 (5.0×10$^3$) 432 (5.8×10$^4$).

Nickel derivative: UV-visible ($H_2O$ at 14.3×10$^{-6}$M) $\lambda(\epsilon)$ 568 (4.9×10$^3$) 530 (1.0×10$^4$) 417 (1.1×10$^5$).

e) Alternative preparation of 5-(4-aminophenyl)-10, 15, 20-tris (N-methyl-4-pyridyl)-porphyrin triacetate by methylation of porphyrin (a) followed by reduction of the nitro function.

To 0.016 (0.024 mmole) of porphyrin (a) in 20 ml of DMF, a large excess of methyl iodide (1 ml) is added. The mixture is stirred for 2 hours at 40° C., then the solvent is evaporated to dryness. The residue is taken up in 3 ml of 6N hydrochloric acid. After addition of dihydrated stannous chloride, stirring is maintained at ambient temperature for 15 hours. Then the solvent is evaporated to dryness. The residue is taken up in methanol.

The addition of filtered ion exchange resin (Amberlite IRN 78) in the acetate form (4 eq.) to this solution, followed by stirring for 3 hours at ambient temperature leads to the corresponding acetate after filtration followed by evaporation of the solvent. The residue is taken up in water and, after one passage through a LH2O column, the porphyrin is purified. Yield=83%. The structural formula of this compound (X=$CH_3COO$) is shown on the appended drawing.

$^1$H NMR (CD$_3$COOD) $\delta$ 9.51 (M, 6H, protons 2,6 pyridine); 9.04 (m broad, 14H, $\beta$-pyrrole and protons-3,5-pyridine), 8.95 (m, 2H, protons-2,6-4-amino-phenyl), 7.8 (m, 2H, protons-3,5 4-amino-phenyl); 4.92 (m, 9H, N-methyl-4-pyridyl).

f) 5-(4-trimethylaminophenyl)-10, 15, 20-tris (N-methyl-4-pyridyl) porphyrin iodine.

To 0.014 g (0.02 mmole ) of the porphyrin (b) 4 ml of DMF, 0.014 ml (0.2 mmole, 10 eq.) of methyl iodide are adder dropwise and the mixture is refluxed for 3 hours. The solution is then stirred at ambient temperature for 15 hours, then the solvent is evaporated to dryness. The residue is triturated with dichloromethane, methanol, and then with acetone. After being filtered off, the product is dried in a vacuum. Product isolated=0.019 g; yield=83%.

UV-visible (MeOH/AcOH): 99.1) $\lambda$ ($\epsilon$) : 655 (1.3×10$^3$); 590 (4×10$^3$); 560 (4×10$^3$); 515 (1.3×10$^4$); 421 (7.0×10$^4$) (Soret band).

Mass (FD) : m/e=660

$^1$H NMR (DMSOd$_6$ at 303K) $\delta$ : 9.60 (d, 6H, J=5.9 Hz, p-2,6-pyridine); 9.27 (m, 8H, $\beta$pyrrole); 9.13 (d, 6H, J=5.9 Hz, p-3,5-pyridine); 8.18 (d, 2H, J=8.6 Hz, p-2,6 of 4-aminophenyl); 7.34 (d, 2H, J=8.6 Hz, p-3,5 of 4-aminophenyl); 4.86 (s broad 9H, N-methyl-4-pyridyl); 3.46 (s, 9H, N ($CH_3$)$_3$: −2.73 (s, NH pyrrole).

g) Manganese (III) 5-(4-trimethylaminophenyl)-10, 15, 20-tris (N-methyl-4 pyridyl)-porphyrin pentaacetate.

To 0.053 g (0.05 mmole) of the porphyrin iodide (f) in 4 ml of DMF are added 0.062 ml (0.047 mmole), 10 eq.) of 2, 4, 6-collidine followed by 0.047 mmole (10 eq.) of manganese acetate, Mn ($CH_3COO$)$_2$, $4H_2O$. The mixture is refluxed for 3 hours and then is stirred for 15 hours at ambient temperature. The solvent is evaporated to dryness and the residue is washed with water, then taken up in methanol. The addition of anhydrous ion exchange resin of the Amberlite IRN 78 type in the acetate form (4 eq.) to this solution, followed by stirring for 3 hours at ambient temperature, makes it possible to obtain the acetate derivative of the title after filtration followed by evaporation of the solvent. The product is then purified by precipitation from a methanol/acetone mixture, Yield=80%. M.p. higher than 240° C.

h) Alternative preparation by reversal of the preceding steps (f) and (g).

To 0.030 g (0.05 mmole of deprotected porphyrin (c) in 3 ml of DMF, are added 0.062 ml (0.047 mmole, 10 eq.) of 2, 4, 6-collidine followed by 0.047 mmole (10 eq.) of a salt of manganese, $Mn(CH_3COO)_2$, $4H_2O$, of iron or zinc. The mixture is refluxed for 3 hours and then stirred at ambient temperature for 15 hours. The solvent is evaporated to dryness and the residue is washed with water then purified on a dry column of neutral alumina (eluant: dichloromethane followed by dichloromethane/ethanol). To the metalloporphyrin thus obtained in 3 ml of DMF, methyl iodide (10 eq.) is added and the mixture is refluxed for 4 hours, then stirred at ambient temperature for 15 hours. The mixture is then evaporated to dryness and taken up in methanol. The addition of filtered ion exchange resin of the Amberlite IRN 78 type in the acetate form (4 eq.) to this solution followed by stirring for 3 hours at ambient temperature leads to the acetate derivative of the title after filtration followed by evaporation of the solvent. The product is then purified by precipitation from a methanol/acetone mixture. Yield=82%. In the same manner, the corresponding iron and zinc derivatives were obtained by replacing manganese acetate by $FeCl_2$, $4H_2O$ or $Zn(CH_3COO)_2$, $2H_2O$ (10 eq. each time), respectively.

EXAMPLE 2

Hydroxyphenyl Derivatives of Porphyrin i) 5-(4-hydroxyphenyl)-10, 15, 20-tris (4-pyridyl)-porphyrin.

A mixture of 3.19 g (0.026 mole; 1.75 eq.) of 4-hydroxy phenyl carboxaldehyde in 205 ml of propionic acid and 10 ml of acetic anhydride is heated at 110° C. with stirring. To this solution is added slowly 4.27 ml (0.045 mole; 3eq.) of 4pyridine carboxaldehyde, followed by 4.13 ml (0.06 mole; 4 eq.) of pyrrole and the mixture is heated at reflux for 1 h 30. Cooled to ambient temperature, the mixture is evaporated to dryness and neutralized with an aqueous solution of ammonia. After being filtered off, the precipitate is washed several times with dichloromethane. The organic phase is then concentrated, then purified on a column of dry silica (eluant: dichloromethane/ethanol 95/5). Isolated product=0.52 g; Yield=5.5%; TLC: $R_f$=0.14 (eluant: $CH_2Cl_2$/ethanol, 95/5).

UV-visible ($7.2 \times 10^{-6}$M in chloroform) λ (ε) 642 ($3.2 \times 10^3$); 587 ($7.9 \times 10^3$); 545 ($9.4 \times 10^3$); 511 ($2.8 \times 10^4$); 416 ($5.1 \times 10^5$) (Soret band).

$^1$H NMR (CDCl$_3$ at 294K) δ 9.04 (d, 6H, J=5.2 Hz, 2,6-pyridine protons); 8.95 (d, 2H, J=4.8 Hz, β-pyrrole); 8.86 (m, 6H, β-pyrrole); 8.20 (d, 2H, J=8.3 Hz, 2,6-phenoxy-4 protons); 816 (d, 6H, J=5.5 Hz, 3,5-pyridine protons); 7.52 (d, 2H, J=8.3 Hz, 3,5-phenoxy-4 protons); 2.80 (q, 2H, J=7.5 Hz, $CH_2CH_3$); 2.50 (m, 2H, OH); 1.42 (t, 3H, J=7.5 Hz, $CH_3CH_2$); −2.89 (s, 2H, pyrrole NH).

Analysis: in the calculations, one molecule of ethanol of solvation is also assumed, $C_{41}H_{27}N_7O$, EtOH. Calculated % : C, 75.96; H, 4.97; N, 14.431. Found % : C, 76.08; H, 4.77; N, 13.09.

j) Cis-5, 10-bis(4-hydroxy-phenyl)-15, 20-bis(4-pyridyl)-porphyrin.

During the purification on a column of dry silica of the reaction mixture of the preceding paragraph, we also obtain the cis-5, 10-bis, (4-hydroxy-phenyl)-15, 20-bis (4-pyridyl)-porphyrin (eluant: $CH_2Cl_2$/EtOH, 97.5/2.5): product isolated=0.74 g; yield=7.7%; TLC: $R_f$=0.21 (eluant: $CH_2Cl_2$/EtOH, 95/5).

UV-visible ($7.2 \times 10^{-6}$M in CHCl$_3$) λ (ε) 642 ($2.1 \times 10^3$); 5.86 ($4.4 \times 10^3$); 546 ($5.8 \times 10^3$); 512 ($1.5 \times 10^4$); 415 ($3 \times 10^5$) (Soret band).

$^1$H NMR (CDCl$_3$) δ 9.03 (d, 4H, J=5.8 Hz, 2,6-pyridine protons); 8.94 (d, 2H, J=4.9 Hz, β-pyrrole); 8.91 (s, 2H, β-pyrrole); 8.84 (s, 2H, β-pyrrole); 8.81 (d, 2H, J=4.9 Hz, β-pyrrole); 8.20 (d, 4H, J=8.5 Hz, 2,6-phenoxy-4 protons); 8.17 (d, 4H, J=5.8 Hz, 3,5 pyridine protons); 7.51 (d, 4H, J=8.5 Hz, 3,5-phenoxy-4 protons); 2.80 (q, 2H, J=7.5 Hz, $CH_2CH_3$); 1.42 (t, 3H, J=7.5 Hz, $CH_3CH_2$); −2.88 (s, 2H, pyrrole NH).

Analysis: in the calculations, it was assumed that there was 1.7 molecules of ethanol of solvation, $C_{42}H_{28}N_6O_2$, 1.75 EtOH, Calculated % : C, 74.95; H, 5.28; N, 11.53. Found % : C, 74.33; H, 4.99; N, 11.23.

k) 5-(4-pyridyl)-10, 15, 20-tris (4-hydroxy-phenyl)-porphyrin.

In the same manner as that previously described, we obtain 5-(4-pyridyl)-10, 15, 20-tris (4-hydroxy-phenyl)-porphyrin (eluant:dichloromethane). Product isolated=0.62 g; yield=6.3%; TLC: $R_f$=0.31 (eluant): $CH_2Cl_2$/EtOH 95/5).

UV-visible ($1.2 \times 10^{-5}$M in CHCl$_3$) λ (ε) 642 ($2.6 \times 10^3$); 587 ($4.4 \times 10^3$); 548 ($5.5 \times 10^3$); 512 ($1.3 \times 10^4$); 416 ($3.3 \times 10^5$) (Soret band).

$^1$H NMR (CDCl$_3$) δ 9.02 (d, 2H, J=5.9 Hz, 2,6-pyridine protons); 8.91 (d, 2H, J=4.9 Hz, β-pyrrole); 8.89 (s, 4H, β-pyrrole); 8.79 (d, 2H, J=4.9 Hz, β-pyrrole); 8.20 (d, 6H, J=8.4 Hz, 2,6-phenoxy-4 protons); 8.16 (d, 2H, J=5.9 Hz, 3,5-pyridine protons); 7.51 (d, 6H, J=8.4 Hz, 3,5-phenoxy-4 protons); 2.79 (q, 2H, J=7.5 Hz, $CH_2CH_3$); 1.58 (m, 6H, OH); 1.42 (t, 3H, J=7.5 Hz, $CH_3CH_2$); −2.86 (s, 2H, pyrrole NH).

Analysis: in the calculations, it was assumed that there was two molecules of ethanol of solvation, $C_{43}H_{29}N_6O_3$, 2 EtOH, Calculated % : C, 74.67; H, 5.47; N, 9.27. Found % : C, 74.49; H, 5.06; N, 8.45.

l) Manganese 5-(4-hydroxyphenyl)-10, 15, 20-tris (4-pyridyl)-porphyrin acetate.

The metalation reaction is carried out according to the same procedure as described for the porphyrin (g) of example 1.

Mass (FAB+) : m/e 687 (M+).

m) 5-(4-hydroxyphenyl)-10, 15, 20-tris (N-methyl-4-pyridyl)-porphyrin.

The methylation of the porphyrin of example (i) by means of methyl iodide in DMF, followed by an exchange of iodide ions for acetate ions and is performed according to the method described in example (f). (yield=88%).

$^1$H NMR (CD$_3$COOD) δ 9.46 (m, 6H, 2,6-pyridine protons); 9.35 (m, 2H, β-pyrrole); 9.14 (m, 4H, β-pyrrole); 8.99 (m, 6H, 3,5-pyridine protons); 8.71 (m, 2H, β-pyrrole; 8.15 (d, 2H, J=7.6 Hz, 2,6-phenoxy-4 protons); 7.56 (d, 2H, J=7.6 Hz, 3,5-phenoxy-4 protons); 4.91 (s broad, 9H, N—Me).

n) Manganese (III) 5-(4-hydroxyphenyl)-10, 15, 20-tris (N-methyl-4-pyridyl)-porphyrin tetraacetate the metalation of the porphyrin (i) with manganese acetate, followed by a methylation reaction by means of methyl iodide are performed under the same conditions as for example 1 (h) and after the exchange of the counter-ions from iodide into acetate on an ion exchange resin, the expected product is obtained.

Product isolated: 0.018 g; yield=76%.

UV-visible ($6.1 \times 10^{-6}$ M in $H_2O$) $\lambda$ ($\epsilon$) 600 ($2.9 \times 10^3$); 560 ($6.6 \times 10^3$); 464 ($7.3 \times 10^4$) (Soret band).

EXAMPLE 3

Amino-Propyloxyphenyl Derivatives of Porphyrin o) 5-[4-(3-amino-propyloxy)-phenyl]-10, 15, 20-tris (4-pyridyl)-porphyrin.

To a solution of 0.051 g (0.8 mmole) of the porphyrin of example (i) in 3 ml of DMF are added at ambient temperature 0.65 g (16.4 mmole; 20.5 eq.) of powdered sodium hydroxide. The colour of the solution changes from violet to green and the mixture is stirred for 15 minutes. 0.017 g (0.88 mmole; 1.1 eq.) of 3-bromo propylamine hydrobromide are added to this solution and stirring is maintained for 3 h. The progress of the reaction is followed by TLC (silica plate; eluant: $CH_2Cl_2$/EtOH, 50/50). After this time, 0.017 g of 3-bromo propylamine hydrobromide are again added and the mixture is stirred for a further 2 h. 2 ml of methanol and 5 ml of distilled water are then added to the reaction mixture. The solution obtained is extracted with dichloromethane. The organic phase is washed with distilled water (twice), dried over sodium sulfate and evaporated to dryness. The product is purified by chromatography on a dry column of basic alumina (eluant: methanol/acetic acid 80/20); product isolated=0.095 g; yield=85%. TLC: $R_f$=0.29 (eluant:$CH_2Cl_2$/EtOH, 80/20 with 1% of $NH_4OH$).

UV-visible ($1.33 \times 10^{-5}$M in methanol) $\lambda$ ($\epsilon$) 642 ($1.6 \times 10^3$); 583 ($3.1 \times 10^3$); 544 ($3.8 \times 10^3$); 510 ($9.8 \times 10^3$); 412 ($1.8 \times 10^5$) (Soret band).

$^1$H NMR (MeOHd$_4$ at 294K) $\delta$ 8.98 (d, 6H, J=5.5 Hz, 2,6-pyridine protons); 8.97 (m, 8H, $\beta$-pyrrole); 8.25 (d, 6H, J=5.5 Hz, 3,5-pyridine protons); 8.18 (d, 2H, J=8.5 Hz, 2,6-phenoxy-4 protons); 7.47 (d, 2H, J=8.5 Hz, 3,5-phenoxy-4 protons); 5,0 (m, 2H, $NH_2$); 4,53 (t, 2H, J=5.6 Hz, $OCH_2$); 3.4 (m, 2H, $CH_2N$); 2.45 (qunituplet, 2H, J=5.5 Hz, $CH_2$).

Mass (DCI/$NH_3$): m/e=692 ($M^+$+H); fragments : 634 ($M^+$—$(CH_2)_3NH_2$).

p) Cis-5, 10-bis/4-(3-amino-propyloxy)-phenyl/-15, 20-bis (4-pyridyl)-porphyrin.

By following the same procedure as that described in example (o) but starting from the porphyrin (j), we obtain the dipyridyl porphyrin bearing 2 arms in the cis position.

Product isolated=0.066 g; yield=79%; TLC : $R_f$=0 (eluant : $CH_2Cl_2$/EtOH, 80/20).

UV-visible ($9.2 \times 10^{-6}$M in MeOH/$CHCl_3$, 95/5) $\lambda$ ($\epsilon$) 644 ($2.2 \times 10^3$); 588 ($3.3 \times 10^3$); 548 ($4.9 \times 10^3$); 512 ($9.2 \times 10^3$); 414 ($1.8 \times 10^7$) (Soret band).

$^1$H NMR ($CDCl_3$) $\delta$ 9.01 (d, 4H, J=5.8 Hz, 2,6-pyridine protons); 8.92 (d, 2H, J=4.9 Hz, $\beta$-pyrrole); 8.89 (s, 4H, $\beta$-pyrrole); 8.81 (s, 2H, $\beta$-pyrrole); 8.77 (d, 2H, J=4.9 Hz, $\beta$-pyrrole); 8.14 (d, 4H, J=5.8 Hz, 3,5-pyridine protons); 8.08 (d, 4H, J=8.4 Hz, 2,6-phenoxy-4 protons); 7.27 (d, 4H, J=8.4 Hz, 3,5-phenoxy-4 protons); 4.32 (t, 4H, J=5.9 Hz, $OCH_2$); 3.08 (t, 4H, J=6.0 Hz, $CH_2N$); 2.32 (m, 4H, $CH_2$); —2.84 (s, 2H, pyrrole NH).

Mass (DCI): m/e 765 ($M^+$+2); fragments at 707 and 649.

Analysis: in the calculations, it was assumed that there was three molecules of ethanol of solvation, $C_{48}H_{42}N_8O_2$, 2.5 EtOH, Calculated % : C, 72.48; H, 6.55; N, 12.76. Found % : C, 72.00; H, 6.67; N, 12.44.

q) 5-/4-(N-trimethyl-3-aminopropyloxy) phenyl/-10, 15, 20-tris (N-methyl-4-pyridyl) porphyrin tetraacetate.

The methylation of the porphyrin (i) by the method already described in example (1f), followed by exchange of the counter-ions from iodide to acetate leads to the corresponding product; yield: 85%.

UV-visible ($4.4 \times 10^{-6}$M in $H_2O$) $\lambda$ ($\epsilon$) 640 ($1.8 \times 10^3$); 580 ($6.4 \times 10^3$); 556 ($6.6 \times 10^3$); 518 ($1.3 \times 10^4$); $1.9 \times 10^5$) (Soret band).

$^1$H NMR ($CD_3COOD$) $\delta$ 9.48 (d, 6H, J=5.8 Hz, 2,6-pyridine protons); 9.17 (s broad, 6H, $\beta$-pyrrole); 9.08 (d, 2H, J=4.8 Hz, $\beta$-pyrrole); 9.00 (d, 6H, J=5.8 Hz, 3,5-pyridine protons); 8.27 (d, 2H, J=8.3 Hz, 2,6-phenyl protons); 7.51 (d, 2H, J=8.3 Hz, 3,5-phenyl protons); 4.91 (s broad, 9H, N-Me-4-pyridyl); 4.53 (m, 2H, $OCH_2$); ;3.87 (m, 2H, $NCH^2$); 3.41 (s, 9H,—$NMe_3$); 2.63 (m, 2H, —$CH_2$—).

r) Manganese (III) cis-5, 10-bis/4-N-trimethyl-3-aminopropyloxy)phenyl-15, 20-bis (N-methyl-4-pyridyl) porphyrin pentaacetate.

By following the same procedure as for example (1h), we obtain starting from the compound (j) the porphyrin metalated with manganese and methylated on the pyridine nuclei and bearing two 3-trimethyl-aminopropyloxy arms at the para positions of the phenyl nuclei.

Product isolated=0.015 g; yield=65%.

UV-visible ($9.3 \times 10^{-6}$M in $H_2O$) $\lambda$ ($\epsilon$) 600 ($6.9 \times 10^3$); 564 ($1.1 \times 10^4$); 467 ($8.7 \times 10^4$) (Soret band).

EXAMPLE 4

(Amino-Butyryl) Aminophenyl Derivatives of Porphyrin s) 5-/4-(N-Boc-aminobutyryl) aminophenyl/-10, 15, 20-tris (4-pyridyl)-porphyrin.

In order to synthesize this derivative, an amino acid of the type (N-Boc-$(CH_2)_n$—COOH is to be prepared according to the method described in the following paragraph, here n=3.

N-Boc-4-aminobutyric acid:

To a suspension of 0.4 g (0.004 mole) of 4-aminobutyric acid, 0.155 g (0.04 mole, 1 eq.) of magnesium oxide and 4 ml of 1M sodium hydroxide in a dioxane/water (6/1) mixture are added slowly 0.96 g (0.0044 mole, 1.1 eq.) of di-tert.-butyl dicarbonate. The mixture is stirred for 20 h at ambient temperature. After filtration, the residue is washed with water. The filtrate is concentrated, then water is added. After a washing with ether, the aqueous phase is acidified to pH=2–3 with 10% acetic acid, then extracted with ethyl acetate. The organic phase is dried over sodium sulfate and evaporated to dryness. The orange oil obtained is triturated with hexane, then dried in a vacuum at 60° C. The product obtained is in the form of a white solid.

Product isolate=0.716 g; yield=90%.

IR (KBr disk) v(cm$^{-1}$) 3343 (NH and COOH); 1689 (broad; COOH and COOtBu).

Mass (DCI) : m/e=204 ($M^+$+1); 221 ($M^+$+18).

$^1$H NMR (CDCl$_3$) δ 11.34 (m, 1H, COOH); 3.14 (split t, 2H, J=6.75 Hz, CH$_2$N); 2.36 (t, 2H, J=6.8 Hz, CH$_2$CO); 1.79 (quintuplet, 2H, J=6.8 Hz, —CH$_2$—); 1.41 (s, 9H, tBu).

With the aid of this derivative, the porphyrin (s) may be prepared in the following manner.

To 0.063 g (0.31 mmole, 3.1 eq.) of N-Boc-4-aminobutyric acid in 6 ml of anhydrous dichloromethane, maintained in an ice bath, are added 0.050 ml (0.36 mmole; 4 eq.) of triethylamine, followed by 0.029 ml (0.3 mmole; 3.3 eq.) of ethyl chloroformate and the mixture is stirred at 0° C. for 30 mn. The mixture is then evaporated to dryness, then taken up in 6 ml of dry dichloromethane and cooled in an ice bath. 0.050 ml (0.36 mmole) of triethylamine are added, followed by 0.066 g (0.1 mmole) of the porphyrin of example (lb).

The mixture is stirred at 0° C. for 1 h, then for 2 h at ambient temperature. The solvent is then evaporated to dryness and the residue is washed copiously with distilled water.

The residue is taken up in dichloromethane. This solution is washed with 5% sodium bicarbonate (twice), then with distilled water (3 times). The organic phase is dried over sodium sulfate, then evaporated to dryness. The product obtained is almost pure, but purification on a column : CH$_2$Cl$_2$/EtOH, 99.5/0.5). Product isolated=0.066 g; yield=77%.

Mass (FAB$^+$) : m/e=8.19 (M$^+$+1); fragments : 763 (M-tBu); 719 (M-COOtBu); 633 (M-C(CH$_2$)$_3$NHCOOtBu.

UV-visible (2.04×10$^{-6}$M in CHCl$_3$) λ (ε) 642 (2.9×10$^4$); 586 (5.2×10$^4$); 548 (6.8×10$^4$); 512 (1.6×10$^5$); 418 (1.6×10$^6$) (Soret band).

IR (KBr disk) ν(cm$^{-1}$): 3319 (NH); 1689 (C=O); 1593 (Ar).

$^1$H NMR (CDCl$_3$) δ 9.04 (m, 6H, 2,6-pyridine protons); 8.97 (d, 2H, J=4.9 Hz, β-pyrrole); 8.84 (s, 4H, β-pyrrole); 8.81 (d, 2H, J=4.9 Hz, β-pyrrole); 8.16 (d, 6H, J=5.9 Hz, 3,5-pyridine protons); 8.08 (m, 4H, 4-phenoxy protons); 4.27 (m, 2H, CH$_2$N); 2.57 (t, 2H, J=6.5 Hz, CH$_2$C=0); 2.02 (m, 2H, —CH$_2$—); 1.53 (s, 9H, tBu); −2.90 (s, 2H, pyrrole NH).

t) Manganese (III) 5-/4-(N-Boc-aminobutyryl) aminophenyl/-10, 15, 20-tris-(4-pyridyl)-porphyrin acetate.

The metalation of the porphyrin of example (s) with manganese acetate in DMF according to the method already described in example (lg) leads to the formation of the expected manganese porphyrin.

Product isolated: m=0.024 g; yield=70%.

UV-visible (2.15×10$^{-6}$M in CHCl$_3$) λ (ε) 613 (6.7×10$^4$); 578 (7.4×10$^4$); 475 (8.9×10$^5$) (Soret band).

u) 5-/4-(aminobutyryl)aminophenyl/-10, 15, 20-tris (4-pyridyl) porphyrin.

A solution of 0.027 g (0.03 mmole) of the porphyrin (s) in 14 ml of a 25% solution of trifluoroacetic acid in dichloromethane is stirred for 1 h at ambient temperature. The solvent is then evaporated to dryness. To the residue obtained is added a large excess of anhydrous ether and vigorous stirring is maintained until a copious precipitate is formed. After filtration, the precipitate is dissolved in water, then neutralized with 5% sodium bicarbonate. The aqueous phase thus obtained is extracted with dichloromethane (3 times). The organic phases are pooled, dried over magnesium sulfate, then evaporated to dryness. The product is purified by precipitation with the aid of a dichloromethane/hexane mixture.

Product isolated: m=0.020 g; yield=84%.

UV-visible (3.62×10$^{-6}$M in CHCl$_3$) λ (ε) 645 (1.1×10$^4$); 588 (1.7×10$^4$); 548 (2.2×10$^4$); 513 (3.3×10$^4$); 419 (6.5×10$^5$) (Soret band).

IR (CaF$_2$ disks)$_n$ (cm$^{-1}$) 3200 (NH broad); 1629 (C=0 broad).

Mass (FAB$^+$) : m/e 719 (M+1)$^+$.

$^1$H NMR (CDCl$_3$) δ 9.3 (d, 6H, J=5.1 Hz, 2,6-pyridine protons); 8.83 (m, 8H, β-pyrrole); 8.15 (d, 6H, J=5.1 Hz 3,5-pyridine protons); 7.97 (d, 2H, J=8.1 Hz, 2,6-amino-4-phenyl protons); 7.08 (d, 2H, J=8.1 Hz, 3,5-amino-4-phenyl protons); 3.24 (m, 2H, CH$_2$N); 2.03 (m, 4H, CH$_2$C=0 and —CH$_2$); −2.90 (m, 2H, pyrrole NH).

v) Manganese (III) 5-/4-(trimethylaminobutyryl) aminophenyl/-10, 15, 20-tris (N-methyl-4-pyridyl)-porphyrin pentaacetate.

The metalation of the porphyrin (u) with manganese acetate in DMF, followed by methylation with methyl iodide in DMF (according to the method already described for the example (1h) leads, after exchange of the counter-ions from iodide to acetate, to the corresponding metalloporphyrin.

Product isolated: 0.021 g; yield=87%.

UV-visible (3.76×10$^{-5}$M in H$_2$O) λ (ε) 596 (1.3×10$^3$); 560 (2.8×10$^3$); 462 (2.8×10$^4$) (Soret band).

Mass (FAB$^+$) : m/e 844.

EXAMPLE 5

Preparation of a Hybrid Metalloporphyrin Molecule-Intercalating Agent a) N$^2$-(4-ethoxycarbonylbutyl)-9-methoxy-ellipticinium bromide.

A mixture of 9-methoxy ellipticine*(0.102 g; 0.37 mmole) and ethyl 5-bromovalerate (0.058 ml; 0.37 mmole; 1 eq.) in 2 ml of anhydrous DMF is heated at 120° C. with stirring for 4 hours. Stirring is maintained overnight at ambient temperature then ether is added to the mixture. After being filtered off, the orange powder obtained is washed with ether and dried in a vacuum. The product isolated=0.156 g; yield=87%.

UV-visible (CHCl$_3$) λ (ε): 506 (3.9×10$^3$); 390 (4.15×10$^3$); 348 (3.4×10$^3$); 332 (6.5×10$^3$).

$^1$H NMR (DMSOd$_6$ at 303 K) δ : 10.11 (s, 1H, H$_1$); 8.57 (d, 1H, J=7.1 Hz, H$_3$); 8.43 (d, 1H, J=7.1 Hz, H$_4$); 7.82 (d, 1H, J=1.9 Hz, H$_{10}$); 7.62 (d, 1H, J=8.8 Hz, H$_7$); 7.33 (dd, 1H, J=2.2 Hz, 8.7 Hz, H$_8$); 4.83 (t, 2H, J=7.1 Hz, (CH$_2$)); 4.16 (q, 2H, J=7.1 Hz, (CH$_2$)$_{17}$); 4.02 (s, 3H, CH$_3$O); 3.44 (s, 3H, (CH$_3$)$_{11}$): 2.84 (s, 3H, (CH$_3$)$_5$); 2.53 (t, 2H, J=7.3 Hz, (CH$_2$)$_{15}$); 2.16 (m, 2H, (CH$_2$)$_{13}$); 1.73 (m, 2H, (CH$_2$)$_{14}$); 1.28 (t, 3H, J=7.1 Hz, (CH$_3$)$_{18}$). The carbon atoms of the arm were number from 12 to 18 starting from the nitrogen atom 2 of the 9-methoxy ellipticine (the methyl of ester part having the number 18).

* This compound and its activity have described in particular in J. Le Men et al., Rev. Europ. Etud. Clin. and Biol. 1970, IV, 534–538.

b) N$^2$-(4-carboxybutyl)-9-methoxy-ellipticinium chloride.

0.148 g (0.3 mmole) of ester (a) in 14 ml of 1N hydrochloric acid are heated at reflux with stirring for 3 hours. Stirring is maintained overnight at ambient temperature. The mixture is then evaporated to dryness; the residue is taken up in methanol and the product is precipitated in the form of an orange powder by ether. After filtration, the product is dried in a vacuum. Product isolated=0.125 g; yield=99%. The presence of chloride ions was checked by a test with silver nitrate).

UV-visible (CHCl$_3$/MeOH) λ (ε) : 452 (1.29×10$^3$); 386 (2.5×10$^3$); 321 (1.8×10$^4$).

Mass (DCI) : M+=377 Decomp. 210° C.

$^1$H NMR (DMSOd$_6$ at 303K) δ : 12.19 (s, 1H, COOH); 10.22 (s, 1H, H$_1$); 8.65 (d, 1H, J=7.2 Hz, H$_3$); 8.59 (d, 1H, J=7.2 Hz, H$_4$); 8.05 (d, 1H, J=2.3 Hz, H$_{10}$); 7.73 (d, 1H, J=8.7 Hz, H$_7$); 7.44 (dd, 1H, J=8.7 Hz, J=2.3 Hz, H$_8$); 4.84 (t, 2H, J=7.0 Hz, (CH$_2$)$_{12}$); 4.06 (s, 3H, CH$_3$O); 3.46 (s, 3H, (CH$_3$)$_{11}$); 3.43 (s, 1H, NH); 2.97 (s, 3H, CH$_3$)$_5$); 2.45 (t, 2H, J=7.4 Hz, (CH$_2$)$_{15}$); 2.16 (m, 2H, (CH$_2$)$_{13}$); 1.70 (M, 2H, (CH$_2$)$_{14}$).

The chloride obtained is dissolved in methanol. The addition of anhydrous ion exchange resin of the Amberlite IRN 78 type in the active form (4 eq.) to this solution, followed by stirring for 4 hours at ambient temperature, gives rise to the corresponding acetate after filtration and evaporation of the solvent. The product is then purified by precipitation with a methanol/ether mixture.

IR (NaCl disks): υ$_{CO}$=1656 cm$^{-1}$

UV-visible (CH$_3$OH) λ (ε) : 3.85 (5.7×10$^3$); 318 (5.7×10$^4$).

By following the same procedures of synthesis, we have prepared the bromides of N$^2$-(2ethoxycarbonyl-ethyl)-9-methoxy-ellipticinium and N$^2$-(5-ethoxycarbonyl-pentyl)-9-methoxy-ellipticinium as well as their homologues bearing an acidic function:

b) N$^2$-(2-carboxyethyl)-9-methoxy-ellipticinium chloride

Product isolate: 0.096 g; yield=98%.

UV-visible (2.2×10$^{-5}$ in MeOH) λ (ε) 410 (5.3×10$^3$); 380 (8.0×10$^3$); 305 (6.2×10$^4$): 295 (6.5×10$^4$); 274 (5.9×10$^4$).

$^1$H NMR (MeOH—d$_4$) δ 9.76 (s, 1H, H$_1$); 8.38 (d, 1H, J=7.0 Hz, H$_3$); 8.31 (d, 1H, J=7.0 Hz, H$_4$); 7.78 (d, 1H, J=2.0 Hz, H$_{10}$); 7.54 (d, 1H, J=8.8 Hz, H$_7$); 7.28 (d, 1H, J=8.8 Hz, J=2.0 Hz, H$_8$); 4.98 (m, 1H, (CH$_2$)$_{12}$); 4.02 (s, 3H, MeO; 3.25 (s, 3H, Me$_{11}$); 2.84 (m, 2H, (CH$_2$)$_{13}$); 2.79 (s, 3H, Me$_5$).

d) N$^2$-(5-carboxypentyl)-9-methoxy-ellipticinium chloride.

Product isolate: 0.170 g; yield=99%.

UV-visible (3.3×10$^{-5}$ in MeOH) λ (ε) 440 (2.4×10$^3$); 382 (6.1×10$^3$); 313 (5.5×10$^4$).

Mass (DCI) : M+=391.

$^1$H NMR (DMSO—d$_6$ at 294K) δ 2.24 (s, 1H, COOH); 10,20 (s, 1H, H$_1$); 8.62 (d, 1H, J=7.0 Hz, H$_3$); 8.56 (d, 1H, J=7.0 Hz, H$_4$); 8.02 (d, 1H, J=2.2 Hz, H$_{10}$); 7.72 (d, 1H, J=8.8 Hz, H$_7$); 7.42 (dd, 1H, J=8.8 Hz, J=2.2 Hz, H$_8$); 4.81 (t, 2H, J=7.2 Hz, (CH$_2$)$_{12}$; 4.05 (s, 3H, MeO); 3.44 (s, 3H, Me$_{11}$); 2.95 (s, 3H, Me$_5$); 2.36 (t, 2H, J=7.0 Hz, (CH$_2$)$_{16}$); 213 (m, 2H, (CH$_2$)$_{13}$); 1.70 (m, 2H, (CH$_2$)$_{15}$); 1.47 (m, 2H, (CH$_2$)$_{14}$).

e) 5-{4-[5-(9-methoxy N$^2$-ellipticinium)-butyryl amino]-phenyl}-10, 15, 20-tris-(4-pyridyl) porphyrin chloride.

To 0.054 g (0.13 mmole); 5.4 eq.) of (b) in 2 ml of an anhydrous dichloromethane are added 0.023 ml (0.16 mmole; 6.7 eq.) of triethylamine followed by 0.021 ml (0.22 mmole; 9.1 eq.) of ethyl chloroformate and the mixture is stirred at ambient temperature for 30 m. The mixture is then evaporated to dryness then taken up in 2 ml of anhydrous dichloromethane. 0.023 ml (0.16 mmole) of triethylamine are added followed by 0.015 g (0.024 mmole) of the porphyrin of example 1 b) and the mixture is heated at reflux for 4 hours. The progress of the reaction is followed by TLC. The mixture is allowed to cool to ambient temperature, then the solvent is evaporated to dryness. The residue, taken up in dichloromethane, is purified on a silica plate (eluant: EtOH/CH$_2$Cl$_2$ 20/80) in the absence of light. The product is taken up in methanol and acetic acid. The filtrate is evaporated to dryness, washed with distilled water then dried in a vacuum. Product isolated=0.011 g; yield=45%.

Mass (FD) : M+—H=991

UV-visible (CH$_3$OH/AcOH: 99.1) λ (ε): 318 (7.6×10$^4$); 414 (5.2×10$^4$); 508 (3.7×10$^3$).

$^1$H NMR (DMSOd$_6$ at 303K) δ : 10.32 (s, 1H, H$_1$); 9.16 (d, 6H, J=5.3 Hz, p-2,6-pyridine); 9.01 (m, 8H, β-pyrrole); 8.73 (m, 1H, H$_3$); 8.67 (m, 1H, H$_4$); 8.38 (d, 6H, J=5.3 Hz, p-3,5-pyridine); 8.21 (m, 4H, 4-aminophenyl); 8.09 (s broad, 1H, H$_{10}$); 7.76 (d, 1H, J=8,7 Hz, H$_7$); 7.44 (d broad, 1H, J=8.7 Hz, H$_8$); 4.96 (m, 2H(CH$_2$)$_{12}$; 4.10 (m, 1H, NH); 4.02 (s, 3H, CH$_3$O); 3.53 (s, 3H, Me$_{11}$); 3.01 (s, 3H, Me$_5$); 2.34 (m, 2H, (CH$_2$)$_{15}$; 2.10 (m, 4H, (CH$_2$)$_{13}$ and $_{14}$); —2.90 (s, 2H, pyrrole NH).

f) 5-{4-[5-(9-methoxy N$^2$-ellipticinium)-butyrylamino]phenyl}-10, 15, 20-tris (N-methyl-4-pyridyl)porphyrin tetraacetate.

The residue from the preceding step (e) is taken up in 3 ml of dry DMF, 0.021 ml (0.34 mmole, 10 eq.) of methyl iodide are added and the mixture is refluxed for 3 hours. The mixture is stirred for 15 hours at ambient temperature. The solvent is then evaporated to dryness and the residue is washed several times with water. After being filtered off, the precipitate is triturated with acetone, then filtered and dried in a vacuum. Product isolated=0.041 g; yield=76%.

UV-visible (MeOH) λ (ε): 655 (2.19×10$^3$); 592 (3.433 10$^3$); 555 (5.0×10$^3$); 519 (8.4×10$^3$); 425 (1.00×10$^5$), (Soret band); 318 (5.9×10$^4$).

The exchange of iodide ions for acetate is carried out in good yields starting from a methanolic solution of this product added to an anhydrous ion exchange resin of the Amberlite IRN 78 type in the acetate form. After being stirred for 2-3 hours at ambient temperature, the mixture is filtered and the solvent is evaporated to dryness. The residue is triturated with acetone, filtered off and dried in a vacuum (yield=80%.

UV-visible (MeOH) λ (ε) : 652 (1.7×10$^3$); 9.16 (d, 6H, J=5.1 Hz, p-2,6-pyridine); 9.00 (m, 8H, β-pyrrole); 8.73 (m, 1H, H$_3$); 8.61 (m, 1H, H$_4$); 8.37 (d, 6H, J=5.1 Hz, p-3,5-pyridine); 8.24 (s, 4H, 4-aminophenyl); 8.03 (s, 1H, H$_{10}$); 7.73 (d, 1H, J=8.70 Hz, H$_7$); 7.42 (dd, 1H, 8.7 Hz, J=2.4 Hz, H$_8$); 4.98 (m, 2H (CH$_2$)$_{12}$; 4.01 (s, 3H, OCH$_3$); 3.70 (s, 3H, Me$_{11}$); 3.48 (s, 9H, CH$_3$); 2.98 (s, 3H, Me$_5$): 2.33 (m, 2H, (CH$_2$)$_{15}$; 2.13 (m, 4H, (CH$_2$)$_{13}$ and $_{14}$); 2.03 (s, 3H, CH$_3$COO$^-$); —2.91 (s, 2H, pyrrole NH).

This molecule can be metalated in the same manner as the corresponding porphyrin according to example 1g). However, it is preferable to use the following method combining the steps e) and f) of the present example.

g) general method for the synthesis of water-soluble metalloporphyrins linked to an intercalating molecule consisting of 9-methoxy-ellipticine.

To 0.070 g (0.17 mmole, 4.8 eq.) of (b) in 3 ml of anhydrous dichloromethane, (this is also applicable into (c) and (d)), are added 0.037 ml (0.026 mmole; 7.6 eq.) of triethylamine followed by 0.035 ml (0.37 mmole; 10.6 eq.) of ethyl chloroformate and the mixture is stirred for 30 min at ambient temperature. The mixture is then evaporated to dryness, then taken up in 30 ml of anhydrous dichloromethane. 0/037 ml (0.26 mmole of triethylamine are added followed by 0.022 g (0.35 mmole) of the porphyrin of example 1 b) and the mixture is heated at reflux for 4 h. The mixture is then evaporated to dryness, then taken up in 3 ml of anhydrous DMF, 0.050 ml (0.38 mmole, 11 eq.) of 2, 4, 6-collidine, followed by 0.39 mmole (11 eq.) of a manganese, iron or zinc salt (Mn(CH$_3$COO)$_2$, 4H$_2$O; FeCl$_2$, 4H$_2$O; Zn(CH$_3$COO)$_2$, 2H$_2$O) are added to the solution. The mixture is heated at 140° C. for 3 h, then it is stirred for 15 h at ambient temperature. The solvent is then evaporated to dryness. The residue is washed with distilled water, then purified on a dry column of neutral alumina (eluant: CH$_2$Cl$_2$ followed by CH$_2$Cl$_2$/MeOH).

The metalloporphyrin thus obtained is taken up in 3 ml of anhydrous DMF, Methyl iodide (10 eq.) is added to the solution. The mixture is refluxed for 3 h. then it is stirred at ambient temperature for 15 h. The solvent is evaporated to dryness and the residue is taken up in methanol. The addition of anhydrous ion exchange resin of the Amberlite IRN 78 type in the acetate form (4 eq.) to this solution, followed by stirring for 3 h at ambient temperature, gives rise to the corresponding acetate after filtration followed by evaporation of the solvent. The residue is then washed with dichloromethane, then recrystallized from a methanol/acetone mixture. The yields and the pysico-chemical data for the different hybrid molecules are described below.

"Intercalating agent-metalloporphyrin" hybrid molecules resulting from the coupling between the porphyrin of example (1b and the ellipticinium of example (5b) (length of the arm connecting the two entities is 7 chain links) yield=60–80%.

UV-visible (H$_2$O) λ (ε) for the three metalated hybrid compounds, respectively the derivatives:

(Mn) : 565 (4.8×10$^3$); 465 (3.7×10$^4$), (Soret band), 316 (4.7×10$^4$).

(Fe) : 430 (2.7×10$^4$), (Soret band); 315 (2.3×10$^4$).

(Zn) : 615 (5.01×10$^3$); 570 (9.9×10$^3$); 442 (9.5×10$^4$), (Soret band); 3.15 (6.1×10$^4$).

Mass (FAB+): for (Mn): 1182 and for (Fe): 1183. Since the Mn and Fe metalloporphyrins are paramagnetic, we can only describe the $^1$H NMR spectrum of the (Zn) compound:

$^1$H NMR (DMSOd$_6$ at 303K) δ : 10.24 (s, 1H, H$_1$); 9.54 (d, 6H, J=5.2 Hz, p-2,6-pyridine); 9.10 (s, 4H, 4-aminophenyl); 9.00 (m, 8H, β-pyrrole); 8.62 (m, 2H, H$_3$ and H$_4$); 8.20 (m, 6H, p-3,5-pyridine); 8,09 (s broad, 1H, H$_{10}$); 7.77 (d, 1H, J=8.7 Hz, H$_7$); 7.45 (d, 1H, J=8.7 Hz, H$_8$); 3.03 (s, 3H, Me$_5$); 2.34 (m, 2H, (CH$_2$)$_{15}$), 2.12 (m, 4H, (CH$_2$)$_{13+14}$); 2.02 (s, 3H, CH$_3$COO$^-$).

* "Intercalating agent-metalloporphyrin" hybrid molecules resulting from the coupling between the porphyrin of example (1b) and the ellipticinium of example (5d) (length of the arm connecting the two entities is 8 chain links).

Manganese (III) 5-/4-/6-(9-methoxy-N$^2$-ellipticinium)pentanoyl/amino-penyl/-10, 15, 20-tris-(N-methyl-4-pyridyl)-porphyrin pentaacetate.

Yield=79%.

UV-visible (3.0×10$^{-6}$M in MeOH) λ (ε) 594 (5.3×10$^3$); 554 (1.6×10$^4$); 420 (4.22×10$^5$) (Soret band); 314 (6.3×10$^4$).

Since the resolution in NMR is better, the non-quaternized pyridinium derivative is described:

$^1$H NMR (DMSO—d$_6$ at 330K) δ 10.30 (s, 1H, H$_1$); 9.12 (d, 6H, J=5.00 Hz, 2,6-pyridine protons); 8.94 (m, 8H, β-pyrrole); 8.72 (d, 1H, J=7.10 Hz, H$_3$); 8.62 (d, 1H, J=6.85 Hz, H$_4$); 8.32 (d, 6H, J=5.0 Hz, 3,5-pyridine protons); 7.70 (d, 1H, J=8.70 Hz, H$_7$); 7.39 (d, 1H, J=2.10 Hz, H$_{10}$); 7.70 (d, 1H, J=8.70 Hz, H$_7$); 7.39 (d, 1H, J=8.70 Hz; J=2.20 Hz, H$_8$); 4.93 (m, 2H, (CH$_2$)$_{12}$); 3.98 (s, 3H, MeO); 3.52 (s, 3H, Me$_{11}$); 2.97 (s, 3H, Me$_5$); 2.29 (m, 2H, (CH$_2$)$_{16}$); 1.95 (m, 4H, (CH$_2$)$_{13}$ and 15); 1.65 (m, 2H, (CH$_2$)$_{14}$).

* "Intercalating agent-metalloporphyrin" hybrid molecules resulting from the coupling between the porphyrin of example 3 (o) and the ellipticinium of example (5b) (length of the arm connecting the two entities is 11 chain links).

The corresponding manganese (III) (N-methyl-4-pyridyl) metalloporphyrin:

Yield : 65%

UV-visible (1.1×10$^{-5}$M in H$_2$O) λ (ε) 596 (1.9×10$^3$); 564 (3.6×10$^3$); 464 (3.5×10$^4$) (Soret band); 314 (2.3×10$^4$).

The corresponding zinc (4-pyridyl) metalloporphyrin (since the resolution in NMR is better, the non-quaternized pyridinium derivative is described):

Zn(PP)(py)$_3$:—PH—O—CH$_2$$^{19}$—CH$_2$$^{18}$—CH$_2$-$^{17}$—NH(CO)—CH$_2$$^{15}$—CH$_2$$^{14}$—CH$_2$$^{13}$—CH$_2$$^{12}$—N'-Ellip Yield=60%.

UV-visible (1.6×10$^{-6}$M in MeOH) λ (ε) 596 (6.3×10$^3$); 554 (2.2×10$^4$); 420 (5×10$^5$) (Soret band); 314 (7.5×10$^4$).

Mass (FAB+) : m/e 1114(M+). $^1$H NMR (DMSO—d$_6$ at 303K) δ 10.26 (s, 1H, H$_1$); 9.11 (d, 6H, J=4.65 Hz, 2,6-pyridine protons); 8.93 (m, 8H, β-pyrrole); 8.66 (d, 1H, J=6.75 Hz, H$_3$); 8.58 (d, 1H, J=6.75 Hz, H$_4$); 8.32 (d, 6H, J=4.65 Hz, 3,5-pyridine protons); 8.15 (d, 2H, J=8.45 Hz, 2,6-phenoxy-4 protons); 8.01 (s broad, 1H, H$_{10}$); 7.65 (d, 1H, J=8.60 Hz, H$_7$); 7.43 (d, 2H, J=8.45 Hz, 3,5-phenoxy-4 protons); 7.35 (d, 1H, J=8.8 Hz, H$_8$); 4.88 (m, 2H, (CH$_2$)$_{12}$); 4.39 (m, 2H, (CH$_2$)$_{19}$); 4.00 (s, 3H, MeO); 3.45 (s, 3H, Me$_{11}$); 2.91 (s, 3H, Me$_5$); 2.39 (m, 2H, (CH$_2$)$_{15}$); 2.17 (m, 4H, (CH$_2$)$_{13}$ and $_{18}$); 1.76 (m, 4H, (CH$_2$)$_{14}$ and $_{17}$).

* Hybrid molecules resulting from the coupling between the porphyrin of example 4 (u) and the ellipticinium (5b) (length of the arm connecting the two entities is 12 chain links):

The corresponding manganese (III) (N-methyl-4-pyridyl) metalloporphyrin:

Yield=47%.

UV-visible (1.1×10$^{-5}$M in MeOH) λ (ε) 598 (3.6×10$^3$); 556 (1.3×10$^4$); 421 (2.8×10$^5$); 315 (5.7×10$^4$).

Since the resolution in NMR is better, the non-quaternized pyridinium zinc derivative is described:

Zn(PP) (py)$_3$: —O—NH(CO)—CH$_2$$^{19}$—CH$_2$$^{18}$—CH$_2$$^{18}$—CH$_2$$^{17}$—NH(CO)—CH$_2$$^{15}$—CH$_2$$^{14}$—CH$_2$-$^{13}$—CH$_2$$^{13}$—CH$_2$$^{12}$—N+—Ellip $^1$H NMR (DMSO—d$_6$ at 303K) δ 10.21 (s, 1H, H$_1$); 9.10 (d, 6H, 8.93 (s, 4H, β-pyrrole); 8.89 (d, 2H, J=4.7 Hz, β-pyrrole); 8.63 (d, 1H, J=7.10 Hz, H$_3$); 8.52 (d, 1H, J=7.10 Hz, H$_4$); 8.31 (d, 6H, J=5.60 Hz, 3,5-pyridine protons); 8.19 (s broad, 4H, 4-aminophenyl protons); 7.96 (d, 1H, J=2.10 Hz, H$_{10}$); 7.68 (d, 1H, J=8.78 Hz, H$_7$); 8.38 (d, 1H, J=8.78 Hz, J=2.2 Hz, H$_8$); 4.87 (t, 2H, J=6.80 Hz, (CH$_2$)$_{12}$); 3.99 (s, 3H, MeO); 3.39 (s, 3H, Me$_{11}$); 2.90 s, 3H, Me$_5$); 2.39 (t, 2H, J=6.90 Hz, (CH$_2$)$_{19}$); 2.18 (m, 4H, (CH$_2$)$_{13}$ and $_{18}$); 1.99 (t, 2H, J=6.90 Hz, (CH$_2$)$_{15}$); 1.76 (m, 4H, (CH$_2$)$_{14}$ and $_{17}$.

* Hybrid molecules resulting from the coupling between the metalloporphyrin of example 3 (o) and the ellipticinium of example (5d) (length of the arm connecting the two entities is 12 chain links):

The manganese (III) (N-methyl-4-pyridyl) metalloporphyrin:
Yield=44%.

UV-visible ($5.3 \times 10^{-6}$M in $H_2O$) $\lambda$ ($\epsilon$) 620 ($5.2 \times 10^3$); 674 ($8.5 \times 10^3$); 466 ($7.4 \times 10^4$) (Soret band); 315 ($7.5 \times 10^4$).

The zinc (4-pyridyl) metalloporphyrin:
Yield=41%.

UV-visible ($8.7 \times 10^{-6}$M in MeOH) $\lambda$ ($\epsilon$) 600 (3.7 ($3.7 \times 10^3$); 558 ($1.2 \times 10^4$); 422 ($2.4 \times 10^5$); 316 ($7.6 \times 10^4$).

Since the resolution in NMR is better, the non-quaternized pyridinium zinc derivative is described:

$Zn(PP)(py)_3$: —Ph—O—$CH_2^{20}$—$CH_2^{18}$—NH—(CO)—$CH_2^{16}$—$CH_2^{15}$—$CH_2^{13}$—$CH_2^{12}$—N+—Ellip.

$^1$H NMR (SMSO–$d_6$ at 303K) $\delta$ 10.09 (s, broad, 1H, $H_1$); 9.10 (d, 6H, J=4.30 Hz, 2,6-pyridine protons); 8.97 (d, 2H, J=4.70 Hz, $\beta$-pyrrole); 8.91 (s, 4H, $\beta$-pyrrole); 8.89 (d, 2H, J=4.70 Hz, $\beta$-pyrrole); 8.56 (d, 1H, J=6.10 Hz, $H_3$); 8.43 (d, 1H, J=6.10 Hz, $H_4$); 8.31 (d, 6H, J=4.30 Hz, 3,5)pyridine protons); 8.19 (d, 2H, J=8.40 Hz, 2,6-phenoxy-4 protons); 7.89 (s broad, 1H, $H_{10}$); 7.67 (d, 1H, J=8.50 Hz, $H_7$); 7.42 (d, 2H, J=8.40 Hz, 3,5-phenoxy-4 protons); 7.37 (d, 1H, J=8.50 Hz, $H_8$); 4.79 (m, 2H, $(CH_2)_{12}$); 4.34 (m, 2H, $(CH_2)_{20}$); 3.98 (s, 3H, MeO); 3.27 (s, 3H, $Me_{11}$); 3.01 (s, 3H, $Me_5$); 2.31 (t, 2H, J=6.60 Hz, $(CH_2)_{16}$); 2.13 (m, 4H, $(CH_2)_{13}$ and $_{19}$); 1.78 (m, 4H, $(CH_2)_{15}$ and $_{18}$); 1.50 (m, 2H, $(CH_2)_{14}$.

For none of these compounds has a melting point below 240° C. been observed. Biological activities of the water soluble metalloporphyrins according to the invention.

Biological activities of the water-soluble metalloporphyrins according to the invention.

The cytotoxic activity was determined on murine leukemia cells of the L1210 type according to a method already described (by C. Paoletti, S. Cros eta al., Chem. Bio. Interact, 25, 45 (179). The effect on cell growth is expressed in terms of the dose inhibiting 50% of cell growth ($ID_{50}$). Only the values of $ID_{50}$ lower than 2 $\mu$M can be considered as being significant from the biological point of view.

The results of cytotoxicity are presented in table 1. Only the porphyrin compounds having a central metal capable of attaining high states of oxidation or capable of leading to metal-oxo derivatives in the presence of oxygen or reduced derivatives of oxygen possess appreciable cytotoxicity; this is the case for the complexes of manganese. The compounds metalated with zinc do not have significant toxicity (table 1). The compound metalated with iron possesses a lower toxicity than the analogous compound with manganese.

The most valuable products of this series are the water soluble derivatives of manganese described in the examples with one, two or three pyridinium groups and one, two or three phenyl groups bearing an amine or alcohol function, thus enabling this molecule to be coupled through the intermediary of an arm to another entity ("vector") exhibiting an affinity for the nucleic acids. These metalloporphyrin derivatives can lead to the synthesis of cytotoxic hybrid molecules with a vector (intercalating agent, oligonucleotides, oligopeptides, proteins or fragments of proteins) adapted to the biological target (tumor cells, viruses, . . . ). We have described such examples (intercalating agents) in example 5.

Moreover, these cytotoxic molecules exhibit a nuclease activity toward DNA in vitro. This activity was demonstrated by studying cleavages on the supercoiled form (form I) of the DNA of the bacteriophage OX 174 (see table 2).

The efficacy of cleavage with the compound (1h) possessing three pyridinium groups is very marked. In fact, only 13% of form I remains at the end of 2 min in the presence of 250 nM of the metalloporphyrin and 5 $\mu$M of potassium hydrogen persulfate, $KHSO_5$. The cleavages are single-strand cleavages since the form II (circular duplex DNA with one cleavage) accumulates before being converted to form III (linear duplex DNA). The experimental conditions and the details of the analytical method are given in the reference Fouquet et al. (cf. page 1).

Biological activities of the hybrid molecules.

We have chosen as hybrid molecule a metalloporphyrin (I) linked to an intercalating agent of the pyrido-carbazole series as vector, namely 9-methoxy-ellipticine.

The most cytotoxic hybrid molecule is that in which the central atom is manganese ($ID_{50}$ of the compound (5f)=9.58 $\mu$M, see table 1). The analogous compound with iron is still cytotoxic ($ID_{50}$=3.2 $\mu$M); on the other hand, the toxicity is much weaker when the metal is zinc. This confirms that the metal of the porphyrin part plays an essential role in the expression of the toxicity of these hybrid molecules. This same effect of the central metal has been observed d for the metalloporphyrins without a vector.

It should be noted that the molecule of example 5 still possesses considerable nuclease activity although less than that of example 1h. The almost complete conversion of form I into form II is obtained at a concentration of 4 $\mu$M of compound (5f).

The hybrid molecules according to the invention can be considered as the first biologically active model compounds mimicking bleomycin, an antitumor medicine acting through the oxidative degradation of DNA in the presence of metal salts (Sausville et al., Biochemistry, 17, 2740 (1978).

In conclusion, the water-soluble metalloporphyrins bearing a function for the coupling of vectors according to the invention possess both cytotoxic activity toward tumor cells and a capacity to cleave nucleic acids in vitro.

These two biological activities are conserved when these same metalloporphyrins are connected by the intermediary of an arm to a vector capable of modulating the affinity or the interaction of these cytotoxic molecules with respect to nucleic acids (the vectors may be intercalating agents, the cases described above, oligonucleotides, oligo or polypeptides, or polyamines . . . ).

They represent a new and original series of cytotoxic molecules which have the nucleic acids as their target. The large range of vectors which can be combined with them makes it possible to envisage a cytotoxic activity towards cells of very different types: tumor cells, viruses.

The compounds of the invention can thus be used in therapy, in particular as antitumoral, antileukemic and antiviral agents. Another subject of the invention is pharmaceutical compositions containing these compounds as well as a pharmaceutically acceptable vehicle or excipient.

TABLE 1

IN VITRO EFFECTS ON L1210 CELLS OF SEVERAL COMPOUNDS ACCORDING TO THE INVENTION

| Compound of the example | $ID_{50}$ (μM) |
|---|---|
| 1 h) (Mn) | 0.54 |
| 1 h) (Fe) | 2.1 |
| 1 h) (Zn) | 10.9 |
| 2 n) (Mn) | 0.68 |
| 5 b) | >23 |
| 5 f) (Mn) | 0.58 |
| 5 g) (Mn) | 0.84 |
| 5 f) (Fe) | 3.2 |
| 5 f) (Zn) | >7.5 |

TABLE 2

OBSERVATION OF ENDONUCLEASE EFFECTS BY MEANS OF ELECTROPHORESIS ON AGAROSE GEL

Conditions

1 μM of metalloporphyrin

5 μM $KHSO_5$ pre-incubation time (DNA + metalloporphyrin):

a) 20 min., b) 1 min. time of incubation (with oxidant): 2 min.

| Compound Product | Forms I | II | III |
|---|---|---|---|
| (DNA control) | 85% | 15% | — |
| 1 h) (Mn) (250 nM)[a] | 13% | 78% | 9% |
| 1 h) (Mn) (250 nM)[b] | 63% | 37% | — |
| 1 h) (Fe) (250 nM)[b] | 75% | 25% | — |
| 1 h) (Zn) (250 nM)[b] | 85% | 15% | — |
| 1 h) (Mn) (1 μM)[a] | — | 59% | 41% |
| 5 f) (Mn) (1 μM)[a] | 32% | 65% | 3% |
| 5 f) (Mn) (4 μM)[a] | — | 71% | 10% |
| 5 f) (Fe) (4 μM)[a] | 58% | 31% | — |

We claim:

1. Metalloporphyrin derivatives according to the invention corresponding to the formula:

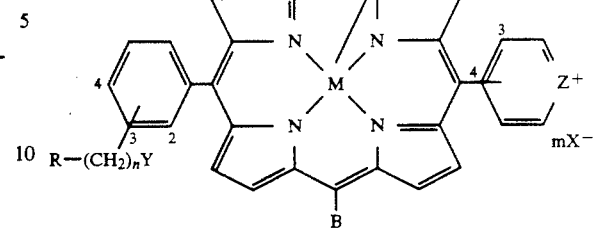

in which A and B each represents:

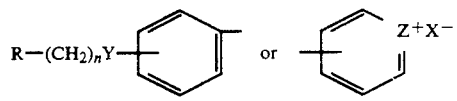

and $Z^+$ represents $N^+—R_1$ or $C—N^+R_1R_2R_3$, $R_1$ being $C_1-C_{10}$ linear or branched aliphatic, and $R_2$ and $R_3$ each being hydrogen or $C_1-C_{10}$ linear or branched aliphatic, R represents $NH_2$, OH, COOH or $—N^+(R_1)_3$ group or a halogen, n is 0 or an integer from 1 to 10, the corresponding alkylene group being either linear or branched, M represents Fe or Mn, $X^-$ represents the anion of a pharmaceutically acceptable carboxylic acid, m being an integer from 1 to 5, and Y represents a bond or a —O—, —CO— or —CONH— radical.

2. Compounds according to claim 1, wherein $R_1$ represents a methyl or ethyl group.

3. Compounds according to claim 1, wherein $R_2$ and $R_3$ are both hydrogen.

4. Compounds according to claim 1, wherein $Z^+$ represents $N^+—R_1$.

5. Manganese (III) 5-(4-aminophenyl)-10, 15, 20-tris (N-methyl-4-pyridyl)porphyrin pentaacetate.

6. Pharmaceutical composition for inhibiting growth of tumor cells, comprising a cytotoxically-effective amount of a compound according to claim 1 and a pharmaceutically acceptable vehicle or excipient.

* * * * *